US006642043B1

(12) United States Patent
Bertino et al.

(10) Patent No.: US 6,642,043 B1
(45) Date of Patent: Nov. 4, 2003

(54) DOUBLE MUTANTS OF DIHYDROFOLATE REDUCTASE AND METHODS OF USING SAME

(75) Inventors: Joseph R. Bertino, New York, NY (US); Emine A. Ercikan-Abali, New York, NY (US); Debabrata Banerjee, New York, NY (US); Shin Mineishi, New York, NY (US); Michel Sadelain, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/142,530

(22) PCT Filed: Mar. 12, 1997

(86) PCT No.: PCT/US97/03873

§ 371 (c)(1),
(2), (4) Date: Jan. 20, 1999

(87) PCT Pub. No.: WO97/33988

PCT Pub. Date: Sep. 18, 1997

Related U.S. Application Data

(60) Provisional application No. 60/013,270, filed on Mar. 12, 1996.

(51) Int. Cl.$^7$ .............................. C12N 1/20; C12N 9/02; C12N 15/00; C07H 21/04; C07K 1/00
(52) U.S. Cl. ................... 435/252.3; 435/189; 435/193; 435/320.1; 536/23.2; 530/350
(58) Field of Search ............................... 435/189, 193, 435/252.3, 320.1; 536/23.2; 530/350

(56) References Cited

FOREIGN PATENT DOCUMENTS

| WO | WO 94/24277 A1 | 10/1994 |
|---|---|---|
| WO | WO 97/33988 A1 | 9/1997 |

OTHER PUBLICATIONS

Rosowsky et al. J. Med. Chem. 38: 745–752, 1995.*
Schweitzer et al. JBC, 264(34) : 20786–95, 1989.*
Huang et al. Biochemistry, 33 : 11576–11585, 1994.*
Accessions XP 003991 and AAA58485.*
Dicker et al. Identification and Characterization of a Mutation in the Dihydrofolate Reductase Gene from the Methotrexate–resistant Chinese Hamster Ovary Cell Line Pro$^{-3}$ Mtx$^{RIII}$. J. Biol. Chem. May 15, 1990, vol. 265, No. 14, pp. 8317–8321, see entire document.
Schweitzer et al. Probing the Role of Two Hydrophobic Active Site Residues in the Human Dihydrofolate Reductase by Site–Directed Mutagenesis. J. Biol. Chem. Dec. 5, 1989, vol. 264, No. 34, pp. 20786–20795, see entire document.

Rosowsky et al. 2,4–diamino–5–substituted–quinazolines as Inhibitors of a Human Dihydrofolate Reductase with a Site–Directed Mutation at Position 22 and of the Dihydrofolate Reductases from *Pneumocystis carinii* and *Toxoplasma gondii*. J. Med. Chem. 1995, vol. 38, pp. 745–752, see entire document.
Banerjee et al. Transfection with a cDNA Encoding a Ser$^{31}$ or Ser$^{34}$ Mutant Human Dihydrofolate Reductase in Chinese Hamster Ovary and Mouse Marrow Progenitor Cells Confers Methotrexate Resistance. Gene. 1994, vol. 139, pp. 269–274, see entire document.
Huang et al. Nonadditivity of Mutational Effects at the Folate Binding Site of *Escherichia coli* Dihydrofolate Reductase. Biochemistry, 1994, vol. 33, No. 38, pp. 11576–11585, see entire document.
Schweitzer et al. Mutations in the Human Dihydrofolate Reductase. In: Chemistry and Biology of Pteridines, Pteridines and Folic Acid Derivatives, 1986, Proceedings of the Eighth International Symposium on Pteridines and Folic Acid Derivatives Chemical, Biological and Clinical Aspects, Montreal Canada. Jun. 15–20, 1986. Edited by: B.A. Cooper and V.M. Whitehead, pp. 793–797, see entire document.
Schweitzer et al. Mutations at Hydrophobic Residues in Dihydrofolate Reductase. In: Chemistry and Biology of Pteridines 1989, Pteridines and Folic Acid Derivatives, Proceedings of the Ninth International Symposium on Pteridines and Folic Acid Derivatives Chemical, Biological and Clinical Aspects, Zurich, Switzerland. Sep. 3–8, 1989. Edited by: H.–Ch. Curtis, S. Ghisla and N. Blau, pp. 760–764, see entire document.
Li et al. Development of a Retroviral Construct Containing a Human Mutated Dihydrofolate Reductase cDNA for Hematopoietic Stem Cell Transduction. Blood. Jun. 1, 1994, vol. 83, No. 11, pp. 3403–3408, see entire document.
Banerjee et al. Molecular Mechanisms of Resistance to Antifolates, A Review. Acta Biochimica Polonica, 1995, vol. 42, No. 4, pp. 457–464, see entire document.
Fan, J. et al. Demonstration of Rb–mediated drug sensitivity and growth inhibition by an inducible expression system. 1995 AACR Abstract Form.
Huang, Zheng et al. Nonadditivity of Mutational Effects at the Folate Binding Site of *Escherichia coli* Dihydrofolate Reductase. Biochemistry 1994, 33, 11576–11585. United States.

(List continued on next page.)

*Primary Examiner*—Tekchand Saidha
(74) *Attorney, Agent, or Firm*—Oppedahl & Larson LLP

(57) ABSTRACT

New mutant forms of human dihydrofolate reductase (DHFR) which have properties superior to the previously disclosed mutants have mutations at both amino acid 22 and amino acid 31. Specific mutant forms are Ser31Tyr22, Ser31Phe22, Gly31Tyr22, Gly31Phe22, Ala31Tyr22 and Ala31Phe22. The mutant DHFR of the invention maybe used as a selectable marker, and to modify the genome of human cells, particularly bone marrow cells or peripheral blood stem cells, to render them resistant to chemotherapy using antifolate agents.

12 Claims, 1 Drawing Sheet

OTHER PUBLICATIONS

Li, Ming–Xia et al. Development of a Retroviral Construct Containing a Human Mutated Dihydrofolate Reductase cDNA for Hematopoietic Stem Cell Transduction. Blood, vol 83, No 11 (Jun. 1), 1994: pp 3403–3408. The American Society of Hematology.

Ercikan–Abali, Emine A. et al. Variants of Human Dihydrofolate Reductase with Substitutions at Leucine–22: Effect on Catalytic and Inhibitor Binding Properties. Molecular Pharmacology, 49:1 (1996). New York, New York.

Oefner, Christian et al. Crystal Structure of Human Dihydrofolate Reductase Complexed with Folate. Received Jan. 20, 1988/Mar. 21, 1988—EJB 880071. Central Research Units, F. Hoffman—La Roche & Co. Ltd, Basel.

Ercikan, E. et al. Effect of Codon 22 Mutations on Substrate and Inhibitor Binding for Human Dihydrofolate Reductase. Chemistry and Biology of Pteridines and Folates, Edited by J.E. Ayling et al., Plenum Press, New York, New York, 1993.

* cited by examiner

Fig. 1A

Introduction of Mutation

| ⌒ = mismatched base | ⟶ = 5' to 3' |
| ⌒ = corrected mismatch | ----- = newly made DNA |

PCR cycle 1

PCR cycle 2

PCR cycle 3

Fig. 1B

Relocation of Mutation

2nd PCR fragment containing mutation at right end (made as above)

mix, denature & anneal region of overlap full duplex molecules
+

+ extension

PCR with outer two primers

DOUBLE MUTANTS OF DIHYDROFOLATE REDUCTASE AND METHODS OF USING SAME

This application is a 371 of PCT/US97/03873, filed Mar. 12, 1997, and claims the benefit of U.S. Provisional Application No. 60/013,270, filed Mar. 12, 1996. +gi The invention described herein was made in the course of work under Grant No. CA-08010 from the National Institutes of Health. The United States government may have certain rights in this invention.

BACKGROUND OF THE INVENTION

This application relates to a new mutants of the enzyme dihydrofolate reductase, and to the use of these mutants as selectable markers and for gene therapy to produce drug resistant bone marrow or peripheral stem cells.

Dihydrofolate reductase (DHFR, 5,6,7,8-tetrahydrofolate:NADP+oxidoreductase, EC 1.5.1.3) catalyzes the NADPH-dependent reduction of dihydrofolate to tetrahydrofolate, an essential carrier of one-carbon units in the biosynthesis of thymidylate, purine nucleotides, serine and methyl compounds. DHFR is an essential enzyme in both eukaryotes and prokaryotes.

In rapidly dividing cells, the inhibition of DHFR results in the depletion of cellular tetrahydrofolates, inhibition of DNA synthesis and cell death. Because of this, folate analogs which inhibit DHFR, for example methotrexate (MTX), are used as antineoplastic agents. The utility of "antifolate" treatments of this type is limited by two factors. First, tumor tissues may rapidly develop resistance to the antifolate, rendering the treatment ineffective. Second, the treatment may be toxic to rapidly dividing normal tissues, particularly to bone marrow or peripheral stem cells.

International Patent Publication No. W094/24277, which is incorporated herein by reference, discloses mutant forms of human DHFR which have increased resistance to inhibition by antifolates used in therapy includi MTX. The specific mutants disclosed differ from wild-type human DHFR as a result of a single mutation occurring at amino acid 15, 31 or 34.

Mutations at amino acid 22 of human DHFR have also been shown to reduce the sensitivity of the enzyme to antifolate inhibition. Ercikan et al., in *Chemistry and Biology of Pteridines and Folates*, J. E. Ayling, ed., Plenum Press (1993). In these mutants, the amino acids isoleucine, methionine, phenylalanine and tyrosine are substituted for the leucine of the wild-type enzyme.

SUMMARY OF THE INVENTION

The present invention provides new mutant forms of human DHFR which have properties superior to the previously disclosed mutants. In particular, the present application is addressed to mutant forms of human DHFR which have mutations at both amino acid 22 and amino acid 31. Preferred mutant forms within the scope of the invention are Ser31Tyr22, Ser31Phe22, Gly31Tyr22, Gly31Phe22, Ala31Tyr22 and Ala31Phe22.

The mutant DHFR of the invention may be used as a selectable marker. Thus, an aspect of the present invention is a method of selecting among clones for the introduction of a non-selectable gene comprising the steps of (a) inserting the non-selectable gene into a DNA vector comprising DNA encoding a mutant form of human dihydrofolate reductase which differs from wild-type human dihydrofolate reductase at both amino acid 22 and amino acid 31, wherein the mutant form has an amino acid with a larger volume side chain than leucine at amino acid 22 and an amino acid having a smaller volume, more hydrophilic side chain than phenylalanine at amino acid 31;

(b) introducing the vector containing the non-selectable gene into cells of a type in which the non-selectable gene and the mutant form of dihydrofolate reductase are expressed; and (c) selecting cells which are resistant to inhibition by antifolates.

The mutant DHFR of the invention may also be used to modify the genome of human cells, particularly bone marrow cells or peripheral blood stem cells to render them resistant to chemotherapy using antifolate agents. Thus a further aspect of the invention is a method for gene therapy comprising the steps of:

(a) obtaining hematopoietic cells from a human patient;

(b) transducing into the hematopoietic cells an expressible mutant form of human dihydrofolate reductase which differs from wild-type human dihydrofolate reductase at both amino acid 22 and amino acid 31, wherein the mutant form has an amino acid with a larger volume side chain than leucine at amino acid 22 and an amino acid which having a smaller volume, more hydrophilic side chain than phenylalanine at amino acid 31; and (c) returning the transduced cells to the human patient.

DESCRIPTION OF THE DRAWING

FIG. 1 shows a method as described by Higuchi et al. for introducing a specific mutation into a DNA sequence during PCR amplification.

DETAILED DESCRIPTION OF THE INVENTION

This application relates to "double-mutants" of human DHFR which differ from wild-type DHFR at both amino acid 22 and amino acid 31.

Wild-type DHFR has a leucine residue at amino acid 22 and a phenylalanine residue at amino acid 31. From studies of the crystal structure of DHFR, the leucine residue has been shown to be close to the active site and has been implicated in the formation of hydrophobic interactions with the folate enzyme substrate. In the mutants of the invention, the leucine residue is replaced with a residue which will disrupt binding of the mutant DHFR to antifolates. In particular, uncharged amino acid residues such as phenylalanine or tyrosine with larger side chains than leucine which will sterically hinder entry of the antifolate to the active site of the enzyme are suitable. Substitution of arginine at this position results in an inactive enzyme. Thus replacement with charged groups would appear to be unsuitable.

The normal phenylalanine residue at amino acid 31 has been shown to interact with the p-aminobenzoyl glutamate moiety of folate or antifolate substrates. Oefner et al., *Eur. J. Biochem* 174: 377–385 (1988). In the mutants of the invention, this phenylalanine is replaced with a small hydrophilic amino acid such as alanine, serine or glycine.

Mutant forms of human DHFR can be produced by site-directed mutagenesis of cDNA encoding wild-type human DBFR using the techniques described by Higuchi et al., *Nucleic, Acids Res.* 16: 7351–7367 (1988), which is incorporated herein by reference. In general, this procedure calls for the use of two sets of primers: a first pair which flanks the entire cDNA of DHFR and which therefore will produce a full length copy of the cDNA upon PCR amplification, and a second pair which are complementary to one another and which contain the desired mutation. These primers initially produce two sets of products, one having the mutation introduced near the 3'-end, and the other having the mutation introduced near the 5'-end. Because these two products are complementary to one another as well as to the PCR primers, however, the two products can form an overlapping duplex which is extended in both directions. Thus, PCR amplification of cDNA in the presence of these two primer sets results in full-length cDNA having the desired mutation as shown in FIG. 1.

In the case of the double mutants of the invention, this procedure is performed twice. First, site-directed mutagenesis is performed to introduce a mutation at one of the two sites and to produce a single-mutant cDNA. This single-mutant cDNA is then subjected to the site-directed mutagenesis procedure a second time to introduce a mutation at the second site. The double-mutants of the invention can also be prepared by first preparing a Ser31 or Gly31 mutant as described in Schweitzer et al., *J. Biol. Chem.* 264: 20786–20795 (1989) and then introducing a mutation at amino acid 22 using the primers shown in Table 1 or primers complementary thereto.

TABLE 1

PRIMERS FOR MUTATION AT AMINO ACID 22

| Introduced Amino Acid | Primer | |
|---|---|---|
| phenylalanine | 5'-CCA GGG TTT GTC CCC GTT-3' | SEQ ID No. 1 |
| tyrosine | 5'-TGG CCA GGG TAC GTC CCC GTT CTT-3' | SEQ ID No. 2 |

Optimal mutants of DHFR for use in gene therapy applications will have two characteristics. First, the mutant should provide levels of DHFR activity with normal substrates which are sufficient to fulfill the function of uninhibited wild-type DHFR. Second, the mutant should continue to have this activity even in the presence of therapeutically effective levels of antifolates used in chemotherapy.

The extent to which a mutant form of DBFR has these characteristics can be preliminarily assessed by in vitro evaluation, of several kinetic parameters, $K_i$, $K_m$, and $k_{cat}$. The first parameter, $K_i$, is the "inhibition constant" and reflects the level of inhibition by a given compound. $K_i$ is obtained from steady state reaction rates observed for mixtures of enzyme, cofactor, 7,8-dihydrofolate (the normal substrate) and variable levels of antifolate. The higher the value of $K_i$, the higher the concentration of antifolate required to inhibit the activity of the enzyme on the normal substrate, Thus, preferred mutant enzymes for use in gene therapy applications will have values of which are higher than those of wild-type DHFR.

$K_m$, or the "Michaelis constant" reflects the ability of an enzyme to convert a given substrate to product. In this case, the substrate is the normal substrate, 7,8-dihydrofolate. $K_m$ is determined using a double reciprocal plot of the initial velocity of the reaction as a function of the concentration of the substrate. Higher values of $K_m$ reflect a decreased affinity for the normal substrate. Thus, preferred mutant enzymes for use in gene therapy applications will have values of $K_m$ which are as low as possible to be comparable to wild-type DHFR.

$k_{cat}$ reflects the catalytic turnover of the enzyme. $k_{cat}$ values are obtained by active site titration experiments using MTX or from activity and total protein measurements of purified enzyme species. Higher values of $k_{cat}$ reflect a greater ability to convert substrate to product, and thus desirable mutant enzymes for use in gene therapy applications will have values of $K_{cat}$ which are higher than those of wild-type DHFR.

The parameters $K_m$ and $k_{cat}$ can be combined to provide a measure of overall catalytic efficiency which is given by $k_{cat}/K_m$. High levels of catalytic efficiency are preferred. Further, the product of the catalytic efficiency and $K_i$ provides an additional indicator of the properties of a mutant enzyme which takes into account the fact that lower levels of catalytic efficiency may be tolerable if the inhibitory effects of the inhibitor are sufficiently low.

Table 2 summarizes these kinetic parameters for several single mutations as well as for double mutations in accordance with the invention.

TABLE 2

KINETIC PARAMETERS OF VARIANTS OF DHFR

| enzyme | $K_m$ (H$_2$folate) ($\mu$m) | $k_{cat}$ (s$^{-1}$) | $k_{cat}/K_m$ (s$^{-1}\mu$m$^{-1}$) |
|---|---|---|---|
| wild type | 0.08 | 12.7 | 159 |
| 31 serine | 0.44 | 7.0 | 16 |
| 22 phenylalanine | 0.16 | 7.4 | 46 |
| 22 tyrosine | 0.15 | 1.5 | 10 |
| 31 serine 22 phenylalanine | 0.44 | 1.6 | 3.6 |
| 31 serine 22 tyrosine | 0.10 | 1.3 | 13 |

Table 3 shows the interaction of these variants of DHFR with the antifolate methotrexate (MTX). As can be seen, the double mutants Ser31Phe22 and Ser31Tyr22 have $K_i$ values which are much greater than those observed for the single mutants, as well as comparable catalytic efficiencies. These enzymes therefore have very high values for $K_i k_{cat}/K_m$ and are superior to the previously described single mutants for purposes of gene therapy to provide resistance to methotrexate toxicity.

TABLE 3

CAPACITY OF VARIANTS TO CONFER MTX RESISTANCE

| enzyme | $K_i$ (MTX) | $k_{cat}/K_m$ ($s^{-1}\mu M^{-1}$) | $K_i\, K_{cat}/k_m$ ($s^{-1}$) | relative |
|---|---|---|---|---|
| wt | 1.2 | 159 | 0.191 | 1 |
| F31S | 239 | 16 | 3.82 | 20.0 |
| L22F | 106 | 46 | 4.88 | 25.5 |
| L22Y | 1980 | 10 | 19.8 | 104 |
| F31S-L22F | 25600 | 3.6 | 92.2 | 483 |
| F31S-L22Y | 12870 | 13 | 167 | 874 |

Table 4 shows $K_i$ values determined for the various forms of DHFR for several other antifolates, namely aminopterin (APT), trimetrexate (TMTX) and piritrexin (PTX). As in the case of methotrexate, the inhibition constant for the double mutants is much higher than that for the single mutants.

TABLE 4

BINDING OF ANTIFOLATES TO VARIANTS OF DHFR

| | $K_i$ (pM) | | |
|---|---|---|---|
| enzyme | APT | TMTX | PTX |
| wild type | 1.8 | 13.0 | 13.2 |
| 31 serine | n.d. | n.d. | n.d. |
| 22 phenylalanine | 212 | 83.3 | 16.0 |
| 22 tyrosine | 1277 | 2514 | 1190 |
| 31 serine 22 phenylalanine | 20600 | 19100 | 6370 |
| 31 serine 22 tyrosine | 11740 | 116000 | 30300 | cDNA encoding mutant DHFR according to the invention can be introduced into hematopoietic stem cells via a retroviral vector to protect these cells from antifolate toxicity. Thus, a further aspect of the present invention is a retroviral vector which expresses a mutant human DHFR differing from wild-type human DHFR at both amino acids 22 and 31. Such vectors are constructed by insertion of full length cDNA encoding the mutant human DHFR into a retrovirus such as Moloney murine leukemia virus-based N2 retroviral vector (MOMLV) modified to contain the SV40 early promoter, MoMLV modified to include the human β-actin promoter, an MFG-based vector which is a splicing vector without selectable marker that bears the MPSV 3'LTR or Gibbon Ape Leukemia Virus (GaLV) retroviral particles with the GaLV envelope. The retroviral vector DNA is then packaged by transfection into a packaging cell line such as GP-E86 cells, an ecotropic packaging line or GP-AM12 cells or PG-13 cells, amphotropic packaging lines, for example by electroporation.

While amphotropic packaging for retroviral vectors has been widely used in hematopoietic gene transfer studies, the receptor for amphotropic viral particles, Ram-1, is expressed at relatively low levels in hematopoietic cells. In contrast, the envelope of the GaLV binds to a receptor, called GLVR 1, which is highly expressed on this cell population. Therefore, one strategy which has been utilized to increase hematopoietic gene transfer efficiency has been to utilize a MoMLV based vector placed in a packaging cell line (called PG13) which produces viral particles with the GaLV envelope. Miller et al., *J. Virol.* 65:2220–2224 (1991). These particles should bind to hematopoietic cells (with their increased GLVR 1 expression) with higher frequency and result in greater transduction efficiency. Riviere et al., *Proc. Nat'l Acad. Sci. (USA)* 92:6733–6737 (1995). Thus, a preferred approach to gene therapy using the mutant DHFR of the invention will make use of packaged retrovirus in PG13 or similar packaging cells which recognized and binds to the GLVR1 receptor.

The packaged retrovirus capable of expressing a mutant DHFR can be used to provide increased antifolate tolerance to patients undergoing antifolate therapy, thus permitting the usage of higher dosages of the antifolate chemotherapeutic agent. Peripheral blood stem cells (PBSC) are harvested by leukapheresis following treatment with G-CSF and optionally with chemotherapy (for example with cyclophosphamide). The CD34-positive population is selected for example with either a Cellpro Ceprate imnnunoaffinity column or immunomagnetic beads. The cells may be prestimulated for 72–96 hours in liquid culture in the presence of IL1, IL3, KL or Flk-2 Ligand. The CD34+ cells are infected by co-culture with the virus-producing cell line for 24 hours with cytokines (except IL1) and polybrene or protamine. After the infection, hematopoietic cells are expanded in vitro in suspension culture with weekly changes of media and growth factors. During this expansion, cells are exposed to the antifolate to be used in therapy to select for drug resistance.

Transduced PBSC CD34$^+$ cells, optionally combined with untransduced CD34+ cells, are returned to the patient by transfusion following high dose chemotherapy. Beginning 24 hr. after transplant, the patient is treated with the antifolate. Relatively low, well-tolerated dosages may be used initially, with increasing dosages being given thereafter in the absence of indications of toxicity.

The use of transduced cells expressing mutant forms of DHFR to increase tolerance to antifolate drug therapy may be used for patients suffering from any type of cancer known to respond to the antifolate. The method of the invention is particularly suitable for use when the patient is suffering from breast cancer or advanced cancer of the head and neck.

In addition to use in gene therapy to provide hematopoietic cells with resistance to antifolate chemotherapeutic agents, the retroviral vectors of the invention may be used as selectable markers to facilitate the introduction of non-selectable genes into cells for therapeutic purposes. Variant forms of DHFR cDNAs are particularly attractive for this purpose, as they are relatively small and thus other genes can be accommodated in retroviral vectors.

EXAMPLE 1

Double-mutant DHFR enzymes in accordance with the invention were created by site-directed mutagenesis. Each of the mutations was introduced separately, using a polymerase chain reaction technique involving two separate sets of primers, one set flanking the entire cDNA of DHFR and the second set being complimentary to each other and containing the desired mutations.

In the first step, a serine residue was introduced at amino acid 31 as described in Schweitzer et al., *J. Biol. Chem.* 264: 20786–20795 (1989) which is incorporated herein by reference. The single-stranded DNA template for the mutagenesis reaction was prepared by cloning the full length wild-type human DHFR cDNA encoding Seq. ID No. 7, (from plasmid pHD80 obtained from Dr. G. Attardi, California Institute of Technology) in M13mpl 8. Site-directed mutagenesis was carried out using the Oligonucleotide-directed In Vitro Mutagenesis System by Amersham. Phosphorylation of the mutagenic oligonucleotide, annealing of the oligonucleotide with the DNA template, extension of the oligonucleotide with the Klenow fragment of DNA Polymerase I with α-thio-dCTP in place of dCTP, filtering of the reaction mixture to remove single-stranded DNA, nicking the non-mutant strand with the restriction enzyme NcoI (which cannot digest phosphorothioate DNA), removal of the nicked strand with exonuclease III, and repolymerization with *E. coli* DNA polymerase I were all carried out in accordance with the instructions of the manufacturer to produce S31 mutant DHFR.

Mutated CDNA was isolated from M13mp18 by digestion with NcoI and HindIII and ligated into a pKT7 vector fragment formed by digestion of pKT7HDR with NcoI and HindIII. The ligation mixture was transformed into *E. coli* BL21

S31 mutant DHFR was then used as the template for the introduction of a mutation at amino acid 22 using the same basic procedure. To introduce phenylalanine at this position, the complementary primers used were 5'-CCAGGGTTTGTCCCCGTT-3' and SEQ ID No. 1

3'-GGTCCCAAACAGGGGCAA-5', SEQ ID No.3 the mutated regions being shown underlined. To introduce a tyrosine at amino acid 22, the complementary primers used were 5'-TGGCCAGGGJGTCCCCGTTCTC-3' and SEQ ID No. 2

3'-ACCGGTCCCALGCAGGGGCAAGAA-5'. SEQ ID No. 4

The PCR products were digested with NcoI/HindIII sites and subcloned into a pKT7 bacterial expression vector containing the same restriction sites. The resulting ligation mixtures were used to transform *E. Coli* BL21 to express the enzymes to be characterized.

EXAMPLE 2

Gly31Phe22 and Gly31Tyr22 mutants of DHFR were prepared by a single-stranded DNA technique using the TRANSFORMER™ site-directed mutagenesis kit (Clonetech). Two oligonucleotides were synthesized. The first was a mutation primer containing the desired G31 mutation. This primer had the sequence 5'G CTC AGG AAT GAA GGC AGA TAT TTC CAG 3' SEQ ID No. 5 where the underlined portion is the mutation site. The second was a selection primer designed to destroy the unique PvuII restriction site and to create a unique KspI site on the pKT7 vector. The selection primer had the sequence 5'CGC GCG AGG CCG CGG CGG TAA AGC 3'. SEQ ID No. 6 These two primers were annealed to a single-stranded pKT7 vector containing either the Phe22 or the Tyr22 mutant DHFR cDNA and a second srand was synthesized which contained both desired mutations. The reaction mixture containing the two strands was digested with PvuII and then transformed into repair deficient BMH 71-18 mutS cells. The transformed bacteria was used to prepare plasmid. To increase the transformation efficiency of the DNA containing the double mutants, plasmid preparations containing a mixture of single mutations and double mutations was linearized with PvuII. This reaction mixture was then transformed into *E. coli* DH5α. The resulting colonies were screened using KspI digestion which only cuts plasmids containing the double mutant.

EXAMPLE 3

Enzyme expressed by the transformed *E. coli* was purified using an MTX-affinity column, followed by DEAE-Sephacel column chromatography. The purified enzymes were characterized to evaluate their kinetic parameters, and the results are summarized in Table 2.

EXAMPLE 4

MFG Retroviral vectors containing mutant forms of DHFR can be constructed using the methods described by Riviere et al., *Proc. Nat'l Acad. Sci. (USA)* 92: 6733–6737 (1995) for human adenosine deaminase. To form the vector, 396 bp of 5' murine chromosomal DNA, an entire Moloney murine leukemia virus 5'LTR and adjacent sequence up until the NarI site at nt 1035, a sequence containing the viral 3' splice acceptor and spanning nt 5401–5780, having the A nucleotide of the NlaI site changed to C to create a NcoI site at the end of the this fragment, mutant human DHFR cDNA, MoMLV proviral sequences extending from the ClaI site at nt 7674 to the end of the 3' MoMLV LTR, and 695 bp of 3' murine chromosomal DNA are inserted into between the HindIII and EcoRI sites of plasmid pBR322.

EXAMPLE 5

After the viral constructs are made, GP-E86 cells, an ecotropic packaging line, and GP-AM12 cells, an amphotropic packaging line, are co-transfected with each vector using lipofection (DOTAP (Boehringer Mannheim, Germany)). Colonies are selected with G418. Surviving GP-E86 cells are collected, replated, and the supernatant is harvested, centrifuged at 3,000 rpm for 15 minutes to remove cell debris, and frozen at −80C until use. G418 resistant GP-AM12 colonies are expanded, and supernatant subjected to titer measurement by infecting NIH 3T3 cells, using MTX as a selective agent. Briefly, $1\times10^5$ cells/60 mm plate is exposed to appropriate dilutions of viral supernatant in the presence of 8 µg/ml of polybrene for 3 hours. Twenty-four hours later, transduced cells are exposed to 150 nM of MTX or 750 µg/ml of G418. Two weeks later, surviving colonies are counted and the titer calculated as cfu (colony-forming units)/ml of supernatant. The highest titer colonies for each vector are used as an amphotropic producer line. Also, the highest titer colonies of the amphotropic producer line are superinfected with ecotropic supernatants containing the same vector twice and if the titer increases, thesetresultant cells are used as producer lines.

EXAMPLE 6

To confirm the effectiveness of mutant DHFR in accordance with the invention to confer resistance to antifolate toxicty, iii viiio experiments were conducted in mice using the Phe22/Ser31 (F/S) DHFR mutant. Bone marrow cells harvested from 5-fluorouracil treated donor mice were cocultured with virus producing AM12 cells producing SFG-F/S-Neo or SFG-Neo as a control for 24 hours. These cells were transplanted into both irradiated and nonirradiated recipients ($2\times10^6$ and $2\times10^7$ cells per recipient). Bone marrow transplant recipients were challenged with a single dose of 300 mg/kg MTX during each of weeks 4 and 6 post transplant, and with a single dose of 600 mg/kg MTX during each of weeks 6 and 7 post transplant. The recipients were monitored for survival, white blood cell counts, platelet counts, reticulocyte counts and drug resistant CFU-GM colonies. The observations indicated that recipient mice were protected from high dose MTX toxicity, while control animals could not tolerate high MTX doses. Further, it was observed that mDHFR CDNA transduced marrow cells are engraved in both irradiated and nonirradiated recipients.

EXAMPLE 7

Bone marrow from primary transplant recipients was transplanted to secondary recipients, which were in turn tested for resistance to MTX toxicity using a CFU-GM assay. The results, which are summarized in Table 5, showed that protection against MTX toxicity can indeed be transferred, suggesting that an early progenitor cell population was transduced. PCR analysis demonstrated the presence of $Neo^R$ cDNA in CFU-S colonies from secondary recipients.

TABLE 5

| Transduced with | Colonies (in the absence of drug) | Colonies in G418 (750 ug/ml G418) | Colonies in MTX ($2 \times 10^{-8}$M MTX) |
| --- | --- | --- | --- |
| Normal Bone Marrow | 92 | 0 | 0 |
| SFG-Neo | 88 | 26 (30%) | ND |
| SFG-F/S-Neo | 104 | 47 (45%) | 27 (26%) |

What is claimed is:

1. A mutant form of human dihydrofolate reductase having activity as a dihydrofolate reductase, said mutant form differing from wild-type human DHFR as defined by Seq. ID No. 7 as a result of a set of mutations comprising a first mutation wherein an uncharged amino acid with a larger volume side chain than leucine is introduced at the amino acid corresponding to amino acid 22 in the wild-type sequence and a second mutation wherein an amino acid which has a smaller volume, more hydrophilic side chain than phenylalanine is introduced at the amino acid corresponding to amino acid 31 in the wild type sequence.

2. The mutant form of human dihydrofolate reductase of claim 1, wherein the first mutation introduces a phenylalanine or tyrosine and the second mutation introduces an alanine, serine or glycine.

3. The mutant form of human dihydrofolate reductase of claim 1, wherein the first mutation introduces a phenylalanine and the second mutation introduces a serine.

4. cDNA encoding a mutant form of human dihydrofolate reductase having activity as a dihydrofolate reductase, said mutant form differing from wild-type human DHFR as defined by Seq. ID No. 7 as a result of a set of mutations comprising a first mutation wherein an uncharged amino acid with a larger volume side chain than leucine is introduced at the amino acid corresponding to amino acid 22 in the wild-type sequence and a second mutation wherein an amino acid which has a smaller volume, more hydrophilic side chain than phenylalanine is introduced at the amino acid corresponding to amino acid 31 in the wild type sequence.

5. The cDNA of claim 4, wherein the first mutation introduces a phenylalanine or tyrosine and the second mutation introduces an alanine, serine or glycine.

6. The cDNA of claim 4, wherein the first mutation introduces a phenylalanine and the second mutation introduces a serine.

7. A DNA vector comprising DNA encoding a mutant form of human dihydrofolate reductase having activity as a dihydrofolate reductase, said mutant form differing from wild-type human DHIFR as defined by Seq. ID No. 7 as a result of a set of mutations comprising a first mutation wherein an uncharged amino acid with a larger volume side chain than leucine is introduced at the amino acid corresponding to amino acid 22 in the wild-type sequence and a second mutation wherein an amino acid which has a smaller volume, more hydrophilic side chain than phenylalanine is introduced at the amino acid corresponding to amino acid 31 in the wild type sequence.

8. A mammalian cell which produces a mutant form of human dihydrofolate reductase having activity as a dihydrofolate reductase, said mutant form differing from wild-type human DHFR as defined by Seq. ID No. 7 as a result of a set of mutations comprising a first mutation wherein an uncharged amino acid with a larger volume side chain than leucine is introduced at the amino acid corresponding to amino acid 22 in the wild-type sequence and a second mutation wherein an amino acid which has a smaller volume, more hydrophilic side chain than phenylalanine is introduced at the amino acid corresponding to amino acid 31 in the wild type sequence.

9. The mammalian cell of claim 8, wherein the cell is a hematopoietic cell.

10. The mammalian cell of claim 9, wherein the cell is a peripheral blood cell.

11. The mammalian cell of claim 8, wherein the first mutation introduces a phenylalanine or tyrosine and the second mutation introduces an alanine, serine or glycine.

12. The mammalian cell of claim 8, wherein the first mutation introduces a phenylalanine and the second mutation introduces a serine.

* * * * *

UNITED STATES PATENT AND TRADEMARK OFFICE
CERTIFICATE OF CORRECTION

| | |
|---|---|
| PATENT NO. | : 6,642,043 B1 |
| APPLICATION NO. | : 09/142530 |
| DATED | : November 4, 2003 |
| INVENTOR(S) | : Bertino et al. |

It is certified that error appears in the above-identified patent and that said Letters Patent is hereby corrected as shown below:

Please insert
Column 1, Lines 8-11: The invention described herein was made in the course of work under Grant No.: CA-08010 from the National Institute of Health. The United States government has certain rights in this invention.

Signed and Sealed this

Sixth Day of May, 2008

JON W. DUDAS
*Director of the United States Patent and Trademark Office*

SEQUENCE LISTING

<160> NUMBER OF SEQ ID NOS: 7

<210> SEQ ID NO 1
<211> LENGTH: 17
<212> TYPE: DNA
<213> ORGANISM: human

<400> SEQUENCE: 1
ccagggtttg tccccgt                                                17

<210> SEQ ID NO 2
<211> LENGTH: 24
<212> TYPE: DNA
<213> ORGANISM: human

<400> SEQUENCE: 2
tggccagggt acgtccccgt tctc                                        24

<210> SEQ ID NO 3
<211> LENGTH: 18
<212> TYPE: DNA
<213> ORGANISM: human

<400> SEQUENCE: 3
ggtcccaaac agggcaa                                                18

<210> SEQ ID NO 4
<211> LENGTH: 24
<212> TYPE: DNA
<213> ORGANISM: human

<400> SEQUENCE: 4
accggtccca tgcaggggca agaa                                        24

<210> SEQ ID NO 5
<211> LENGTH: 28
<212> TYPE: DNA
<213> ORGANISM: human

<400> SEQUENCE: 5
gctcaggaat gaaggcagat atttccag                                    28

<210> SEQ ID NO 6
<211> LENGTH: 24
<212> TYPE: DNA
<213> ORGANISM: human

-continued

```
<400> SEQUENCE: 6
cgcgcgaggc cgcggcggta aagc                                              24

<210> SEQ ID NO 7
<211> LENGTH: 186
<212> TYPE: PRT
<213> ORGANISM: human

<400> SEQUENCE: 7

Val Gly Ser Leu Asn Cys Ile Val Ala Val Ser Gln Asn Met Gly Ile
1               5                   10                  15

Gly Lys Asn Gly Asp Leu Pro Trp Pro Phe Leu Arg Asn Glu Phe Arg
            20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Tyr Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175
Tyr Lys Phe Glu Val Tyr Glu Lys Asn Asp
            180                 185
```